United States Patent [19]

Cipolli et al.

[11] Patent Number: 5,304,646

[45] Date of Patent: Apr. 19, 1994

[54] AMELINIC COMPOUNDS

[75] Inventors: Roberto Cipolli, Novaro; Gilberto Nucida, Milan; Enrico Masarati, Piacenza; Roberto Oriani; Mario Pirozzi, both of Milan, all of Italy

[73] Assignee: Ministero Dell'Universita' E Della Ricerca Scientifica E Tecnologica, Rome, Italy

[21] Appl. No.: 50,987

[22] Filed: Apr. 22, 1993

Related U.S. Application Data

[63] Continuation of Ser. No. 756,920, Sep. 9, 1991, abandoned.

[30] Foreign Application Priority Data

Sep. 11, 1990 [IT] Italy ............................. 21422 A/90

[51] Int. Cl.$^5$ ........................................... C07D 251/48
[52] U.S. Cl. ................................. 544/204; 544/60; 544/113; 544/209; 544/213
[58] Field of Search ................. 544/60, 113, 204, 209, 544/213

[56] References Cited

U.S. PATENT DOCUMENTS 3,261,835 1/1959 Hamm .......................... 260/249.8
3,806,475 4/1974 Narayan et al. .
4,874,420 10/1989 Wroblowsky et al. ............. 544/204

FOREIGN PATENT DOCUMENTS 0631493 11/1961 Canada ............................. 544/204

OTHER PUBLICATIONS

Chemical Abstracts, 173192g, vol. 110, No. 19, May 8, 1989, & Chem. Express, 1988, pp. 423-426, Y. Inoue, et al. "Synthesis of 4-Hydroxy-2-Phenylazo-1,3,5-Triazines by Oxidative Coupling of 2-Hydrazino-4-Hyroxy-1,3,5-Triazines with N,N-Dialkylanilines".
Chemical Abstracts, 213311j, vol. 93, No. 22, Dec. 1, 1980, & Jpn. Kokai Tokkyo Koho 80 69, 139, May 24, 1980, 12 pages, "Silver Halide Photographic Material Backcoating".
Chemical Abstracts, 39407j, vol. 87, No. 5, Aug. 1, 1987, & Heterocycles, 1977, pp. 423-429, T. Tsujikawa, et al., "Photochemical Reactions of 2-Benzylidenehydrazinopyrimidines".
Chemical Abstracts, 141881c, vol. 74, No. 25, Jun. 21, 1971, & Japan 71 04, 171, Feb. 2, 1971, 4 pages, M. Nakanishi, et al., "S-Triazine Derivatives".
Chemical Abstracts, 86965c, vol. 69, No. 21, Nov. 18, 1968, & Chem. Ber., 1968, pp. 3062-3069, H. Bredereck, et al., "Syntheses of Heterocycles, XII. Substituted S-Triazines. Synthesis and Reactions of 6-Hydroxy-2,-4-Bis(Nitramino)-S-Traizine".
Chemical Abstracts, 11003h, vol. 62, No. 9, Apr. 26, 1965, & Brit. J. Pharmacol., 1965, pp. 274-281, R. Angelucci, et al., "Some Aspects of the Metabolism of Triazine Derivatives Active in Experimentally Induced Virus Infections".

Primary Examiner—Mukund J. Shah
Assistant Examiner—Y. N. Gupta
Attorney, Agent, or Firm—Oblon, Spivak, McClelland, Maier & Neustadt

[57] ABSTRACT

Amelinic compounds of general formula (I)

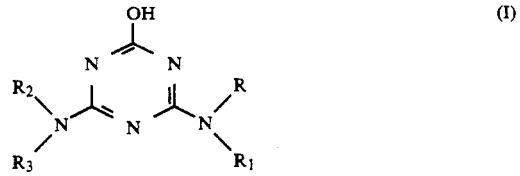

obtained by condensation of 1 mol of cyanuric acid halide with 2 mols of an amine and subsequent hydrolysis of the intermediate thus obtained. Compounds of general formula (I) are used, in particular, as flame retardant additives for polymers.

3 Claims, No Drawings

AMELINIC COMPOUNDS

This application is a continuation of application Ser. No. 07/756,920, filed on Sep. 9, 1991, now abandoned.

The present invention relates to new compounds derived from the 2,4-diamino-6-hydroxy-1,3,5-triazine, able to give high characteristics of self-extinguishing to flame to the thermoplastic polymers or to polymers having elastomeric properties, especially olefin polymers and copolymers.

In particular, are object of the present invention compounds of general formula (I):

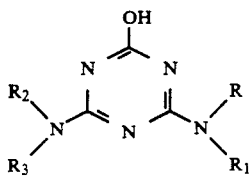

wherein:
R is hydrogen;
and at least one of radicals from $R_1$ to $R_3$ is:

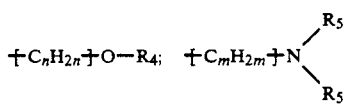

with:
n = integer comprised between 2 and 8;
m = integer comprised between 2 and 6;
$R_4$ = H; $(C_1-C_8)$-alkyl; $(C_2-C_6)$-alkenyl;

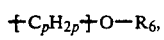

wherein p is an integer comprised between 1 and 4 and $R_6$ is H or $(C_1-C_4)$-alkyl; $(C_6-C_{12})$-cycloalkyl or $(C_6-C_{12})$-alkylcycloalkyl;
radicals $R_5$, equal or different between them, are H; $(C_1-C_8)$-alkyl; $(C_2-C_6)$-alkenyl; $(C_6-C_{12})$-cycloalkyl or $(C_6-C_{12})$-alkylcycloalkyl; $(C_1-C_4)$-hydroxyalkyl; or the group:

is replaced by a heterocyclic radical bound to the alkyl chain through the nitrogen atom and optionally containing another heteroatom preferably selected among O, S and N;
or in the general formula (I) at least one of groups:

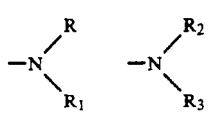

is replaced by a heterocyclic radical bound to the triazine ring through the nitrogen atom and optionally containing another heteroatom preferably selected among O, S and N.

Other radicals from $R_1$ to $R_3$, equal or different among them, have the above-mentioned meaning or are:
H; $(C_1-C_{18})$-alkyl; $(C_2-C_8)$-alkenyl; $(C_6-C_{16})$-cycloalkyl or $(C_6-C_{16})$-alkylcycloalkyl, optionally substituted by a hydroxyl or $(C_1-C_4)$-hydroxyalkyl function;
provided that when $R_2$ and $R_3$ are equal to hydrogen, $R_1$ is different from 2-hydroxyethyl.

Examples of radicals from $R_1$ to $R_3$ in the general formula (I) are: methyl; ethyl; propyl; isopropyl; n-butyl; isobutyl; terbutyl; n-pentyl; isopentyl; n-hexyl; ter-hexyl; octyl; ter-octyl; decyl; dodecyl; octadecyl; ethenyl; propenyl; butenyl; isobutenyl; hexenyl; octenyl; cyclohexyl; propylcyclohexyl; butylcyclohexyl; decylcyclohexyl; hydroxycyclohexyl; hydroxyethylcyclohexyl; 2-hydroxyethyl; 2-hydroxypropyl; 3-hydroxypropyl; 3-hydroxybutyl; 4-hydroxybutyl; 3-hydroxypentyl; 5-hydroxypentyl; 6-hydroxyhexyl; 3-hydroxy-2,5-dimethylhexyl; 7-hydroxyheptyl; 7-hydroxyoctyl; 2-methoxyethyl; 2-methoxypropyl; 3-methoxypropyl; 4-methoxybutyl; 6-methoxyhexyl; 7-methoxyheptyl; 7-methoxyoctyl; 2-ethoxyethyl; 3-ethoxy-propyl; 4-ethoxybutyl; 3-propoxypropyl; 3-butoxypropyl; 4-butoxybutyl; 4-isobutoxybutyl; 5-propoxypentyl; 2-cyclohexyloxyethyl; 2-ethenyloxyethyl; 2-(N,N-dimethylamino)ethyl; 3-(N,N-dimethylamino)propyl; 4-(N,N-dimethylamino)butyl; 5-(N,N-dimethylamino)pentyl; 4-(N,N-diethylamino)butyl; 5-(N,N-diethylamino)pentyl; 5-(N,N-diisopropylamino)pentyl; 3-(N-ethylamino)propyl; 4-(N-methylamino)butyl; 4-(N,N-dipropylamino)butyl; 2-(N,N-diisopropylamino)ethyl; 6-(N-hexenylamino)hexyl; 2-(N-ethenylamino)ethyl; 2-(N-cyclohexylamino)ethyl; 2-(N-2-hydroxyethylamino)ethyl; 2-(2-hydroxyethoxy)ethyl; 2-(2-methoxyethoxy)ethyl; 6-(N-propylamino)hexyl; etc.

Examples of heterocyclic radicals which may replace groups:

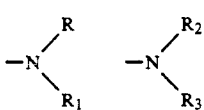

are: aziridine; pyrrolidine; piperidine; morpholine; thiomorpholine; piperazine; 4-methylpiperazine; 4-ethylpiperazine; 2-methylpiperazine; 2,5-dimethylpiperazine; 2,3,5,6-tetramethylpiperazine; 2,2,5,5-tetramethylpiperazine; 2-ethylpiperazine; 2,5-diethylpiperazine; etc.

Examples of heterocyclic radicals which may replace the group:

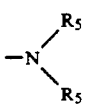

are: aziridine; pyrrolidine; piperidine; morpholine; thiomorpholine; piperazine; 4-methylpiperazine; 4-ethylpiperazine; etc.

Specific compounds comprised in general formula (I) are reported in examples following the present description.

Compounds of general formula (I) may be prepared by hydrolysis reaction of intermediates of general formula (II)

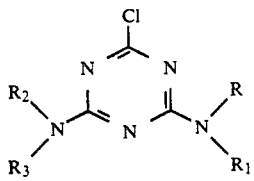

wherein substituents from R to $R_3$ have the previously defined meaning, with an acid (such as for instance hydrochloric acid; hydrobromic acid; sulfuric acid; phosphoric acid, etc.) at temperatures comprised between 60° and 100° C., or with a base (such as for instance sodium hydroxide; potassium hydroxide, etc.) at temperatures comprised between 100° and 180° C.

The product formed can be easily separated from the reaction mass by filtration.

Intermediates of general formula (II) can be easily synthetized by allowing a cyanuric acid halide, for instance the chloride, to react at temperature comprised between 0° and 10° C., in a suitable solvent (such as for instance, acetone, water, methylene chloride, etc.) with an amine of general formula (III):

wherein R and $R_1$ have the previously defined meaning, in the presence or not (according to the used molar ratio) of an acidity acceptor (such as for instance NaOH, NaHCO$_3$, Na$_2$CO$_3$ or triethylamine) thus obtaining the intermediate (IV):

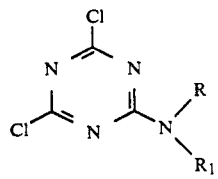

This intermediate, either separated or not, is subsequently allowed to react under conditions analogous to the preceding ones, but working at higher temperature, for instance between 10° and 50° C., with an amine of the general formula (V):

wherein:
$R_2$ and $R_3$ have the previously defined meaning, thus obtaining the intermediate (II).

In the event that intermediates of general formula (II) are desired, wherein groups:

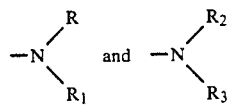

are equal between them, the cyanuric acid halide is allowed to react with two mols (if in the presence of an acidity acceptor) or with four mols (if in absence) of an amine of general formula (III) under working conditions analogous to those previously described.

An alternative method to obtain derivatives of general formula (I) is to subject to hydrolysis reaction, either with an acid, by working at temperature comprised between 80° and 150° C., or with a base by working at temperatures comprised between 100° and 180° C., using the same reagents mentioned for the hydrolysis of intermediates of general formula (II), products of general formula (VI):

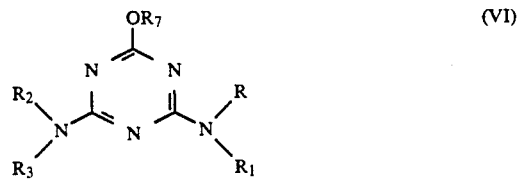

wherein substituents from R to $R_3$ have the previously defined meaning and $R_7$ is preferably ($C_1$-$C_4$)-alkyl.

Products of general formula (VI) can be prepared for instance, by condensation reaction of the intermediate of general formula (II) with a reagent of general formula (VII):

wherein $R_7$ has the previously defined meaning, in a suitable solvent (such as for instance toluene, xylene, orthodichlorobenzene, etc.) or in an excess of the reagent (VII) if it is able to act as solvent also (such as for instance methyl alcohol, ethyl alcohol, etc.), in the presence of a base (such as for instance sodium hydroxide, potassium hydroxide, metal sodium etc.) at temperatures comprised between 60° and 150° C.

Generally products of general formula (I) showing good properties, are obtained in form of white crystalline powder, useable in self-estinguishing polymeric compositions without any further purification.

Examples reported hereinafter illustrate the features of the present invention without limiting the same.

EXAMPLE 1

184.5 g of cyanuric acid chloride and 1300 cc of methylene chloride are introduced in a 2 liter reactor, equipped with stirrer, thermometer, dropping funnel, condenser and cooling bath.

While cooling from the outside, 87.2 g of morpholine and 40 g of sodium hydroxide dissolved in 50 g of water are contemporarily introduce within 3 hours, by keeping the pH comprised between 5 and 7 and the temperature comprised between 0° and 3° C.

The mixture is kept at the temperature of 0°–3° C. for further 3 hours and then the aqueous phase is separated.

After distillation of the methylene chloride 230 g of the intermediate (VIII):

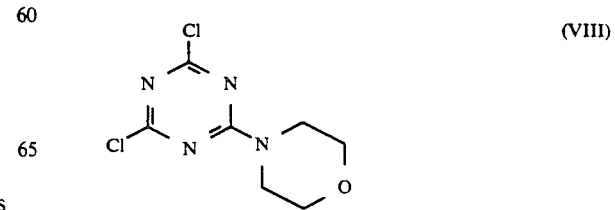

are obtained in form of white crystalline powder; m.p.=155°-157° C. (m.p.=meeting point) and chlorine content equal to 30.12% (theoretical=30.21%).

300 cc of water, 30.5 g of 2-hydroxyethylamine and, under agitation, 117.5 g of intermediate (VIII) are introduced in a 1 liter reactor equipped with stirrer, thermometer, feeding funnel, cooler and heating bath.

The temperature is gradually raised to 40° C.; after 30 minutes the whole is heated to 45° C. and is kept at this temperature for about 3 hours.

The temperature is raised again to 50° C. and a solution consisting of 20 g of sodium hydroxide dissolved in 100 cc of water is added within 3 hours.

The mixture is maintained for further 2 hours at 50° C. and then is heated to 70° C. and is allowed to further react at this new temperature for 30 minutes.

After cooling to room temperature the product formed is filtered and washed on the filter with water.

After drying of the cake in oven at 100° C., 120.3 g of the intermediate (IX):

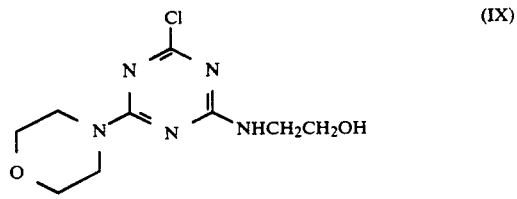

are obtained in form of white crystalline powder; m.p.=172°-173° C. and chlorine content equal to 13.51% (theor. 13.68%).

The structure of intermediates (VIII) and (IX) has been further confirmed by IR spectroscopic analysis.

500 cc of water, 103.8 g of the intermediate (IX) and 79 g of a 37% by weight hydrochloric acid solution are introduced in the same 1 liter reactor.

The mass is heated at 90° C. and is kept at this temperature for 3 hours.

Thereafter the solution is cooled to 50° C. and is neutralized by adding 48 g of sodium hydroxide dissolved in 80 cc of water.

The mass is cooled to 5° C.; the product formed is filtered and washed on the filter with cold water.

After drying of the cake in oven at 100° C., 84.5 g of the product:

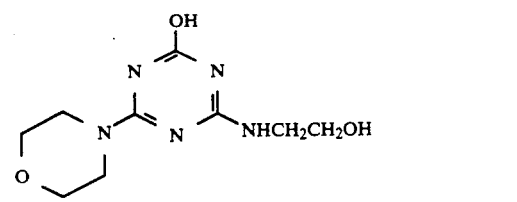

are obtained in form of white crystalline powder; m.p.=251°-253° C.

EXAMPLE 2

800 cc of methyl alcohol, 100 cc of water and 151.2 g of sodium bicarbonate are introduced in a 2 liters reactor equipped as in example 1.

The mixture is cooled to 10° C. and 166 g of the cyanuric acid chloride are introduced.

The temperature is allowed to raise up to 30° C. and is kept at this value for about 1 hour, until the carbon dioxide release is ended. The exothermy itself of the reaction is enough to keep the desired temperature.

The whole is cooled to 5° C. and then 800 cc of cold water are added. The product formed is filtered and washed on the filter.

By drying the cake in oven at 60° C. under vacuum, 123.8 g of the intermediate (X):

are obtained in form of white, crystalline powder; m.p.=90°-92° C. and chlorine content equal to 39.17% (theor.: 39.44%).

400 cc of water and 108 g of the intermediate (X) are introduced in a 1 liter reactor, equipped as in example 1.

The mixture is cooled from the outside to 0°-5° C. and while keeping the temperature at 0°-5° C., 100 g of a 30% by weight ammonia solution are introduced within about 1 hour. The temperature is allowed to spontaneously raise at room temperature and is maintained at this value for 2 hours.

The mixture is cooled to 10° C., the product formed is filtered and washed with cold water. By drying the cake in oven at 100° C., 82. g of the intermediate (XI):

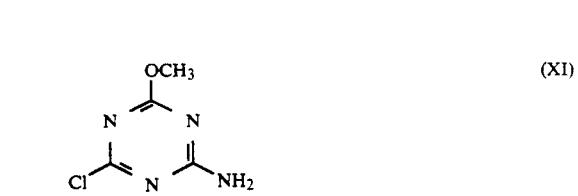

are obtained in form of white crystalline powder; m.p. higher than 300° C. and chlorine content equal to 21.92% (theor.: 22.12%).

The structure of intermediates (X) and (XI) has been further confirmed by NMR analysis.

In the same 1 liter apparatus, but provided with heating bath, there are introduced 300 cc of toluene, 80.2 g of the intermediate (XI) and 90 g of morpholine.

The whole is heated at 60°-65° C. and is kept at this temperature for 2 hours; then it is heated to boiling and is kept under reflux for 1 hour.

The mixture is allowed to cool to room temperature and thereafter the product formed is separated by filtration.

The cake is abundantly washed with water and after having dried, 90.3 g of the intermediate (XII):

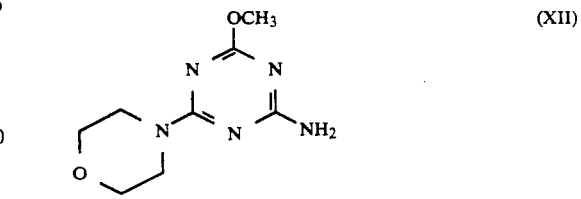

are obtained in form of white crystalline powder; m.p.=182°-184° C.

In the same 1 liter apparatus there are introduced 400 cc of water, 63.3 g of the intermediate (XII) and 59.1 g of a 37% by weight hydrochloric acid solution.

The whole is heated to boiling and is kept under reflux for 2 hours.

After cooling to 80° C., 24 g of sodium hydroxide dissolved in 100 cc of water are added.

The whole is allowed to cool to room temperature and thereafter the product formed is filtered and washed on the filter with water.

By drying the cake in oven at 100° C., 54.7 g of the product:

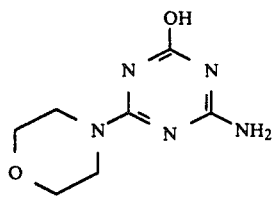

are obtained in form of white crystalline powder; m.p. higher than 300° C.

EXAMPLE 3

600 cc of water and 184.5 g of the cyanuric acid chloride are introduced in a 2 liters reactor equipped as in example 1.

By cooling from the outside to 2° C., 122.5 g of 2-hydroxyethylamine in 100 cc of water are introduced within 2 hours; during the addition the temperature is allowed to gradually raise up to 5°-7° C.

The temperature is raised to 20° C. and is maintained at this value for 1 hour; then the whole is heated at 35°-40° C. and 80 g of sodium hydroxide dissolved in 200 cc of water are added within 3 hours.

The reaction mass is heated at 60° C. and is kept at this temperature for 2 hours.

After cooling to room temperature, the product formed is filtered and washed on the filter.

By drying the cake in oven at 100° C., 203.1 g of the intermediate (XIII):

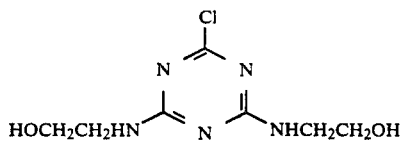

are obtained in form of white crystalline powder; m.p.=188°-190° C.; chlorine content equal to 15.33% (theor. 15.20%).

The structure of the intermediate (XIII) has been further confirmed by IR spectroscopic analysis.

In a 1 liter stainless steel reactor, equipped as in example 1, there are introduced 400 cc of water, 13 g of sodium hydroxide and 70.1 g of the intermediate (XIII).

Then the mixture is heated at 150° C. and is maintained at this temperature for about 10 hours;

After cooling to room temperature, the product formed is filtered and washed on the filter with water.

By drying the cake in oven at 100° C., 57.7 g of the product:

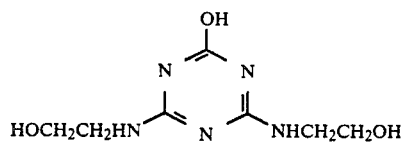

are obtained in form of white crystalline powder; m.p. higher than 300° C.

EXAMPLE 4

In the same 2 liters apparatus as in example 1, there are introduced 1000 cc of methylene chloride and 129.1 g of the cyanuric acid chloride.

By following the modalities described in example 1, 51.2 g of n-butylamine and 28 g of sodium hydroxide in 100 cc of water are fed.

Thereafter, by working as described in example 1, after distillation of the solvent, 148 g of the intermediate (XIV):

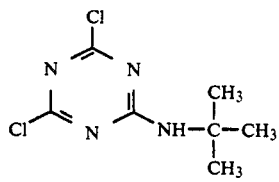

are obtained in form of white, crystalline powder; m.p.=129°-130° C.; chlorine content equal to 31.87% (theor.: 32.13%).

500 cc of chloroform, 110.5 g of the intermediate (XIV) and 30.5 g of 2-hydroxyethylamine dissolved in 80 cc of water are introduced in a 1 liter reactor equipped as in the preceding examples.

The mixture is heated to boiling and is kept under reflux for 3 hours; thereafter, a solution consisting of 20 g of sodium hydroxide in 70 cc of water is introduced within 2 hours.

The boiling is kept for further 1 hour, and thereafter the whole is cooled to room temperature by separating the organic phase.

The solvent is distilled off and the distillation residue is treated with 500 cc of water in the same 1 liter reactor.

After having heated at 50°-60° C. to obtain a good dispersion, the whole is cooled to room temperature and the product formed is separated by filtration.

The cake is washed with water and is dried in oven at 80° C.

106.7 g of the intermediate (XV):

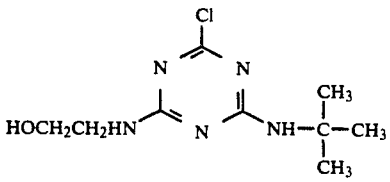

are obtained in form of white crystalline powder; m.p.=134°-135° C.; chlorine content equal to 14.32% (theor. 14.46%)

The structure of intermediates (XIV) and (XV) has been further confirmed by NMR analysis.

500 cc of water, 98.2 g of the intermediate (XV) and 20.5 g of 96% by weight sulfuric acid are introduced in the same 1 liter reactor.

The reaction mass is heated at 85° C. and is kept at this temperature for 2 hours.

Thereafter, within 30 minutes, 32 g of sodium hydroxide dissolved in 100 cc of water are introduced.

After having kept for further 30 minutes at 85° C. the whole is cooled to room temperature and the product formed is filtered and washed on the filter with water.

By drying the cake in oven at 100° C., 83.2 g of the product:

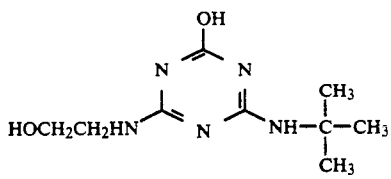

are obtained in form of white crystalline powder having a m.p. higher than 300° C.

EXAMPLE 5

600 cc of water and 184.5 g of cyanuric acid chloride are introduced in a 2 liters reactor equipped as in example 1.

By cooling from the outside to 0°-2° C., 75 g of 2-methoxyethylamine are fed within 1 hour and 30 minutes.

Subsequently, 40 g of sodium hydroxide dissolved in 250 cc of water are fed always keeping the temperature at 0°-2° C. and within 2 hours.

The mass is kept under agitation for further 1 hour at the same temperature then the product formed is separated by filtration and washed on the filter with water.

By drying in oven under vacuum at 60° C., 178.9 g of the intermediate (XVI):

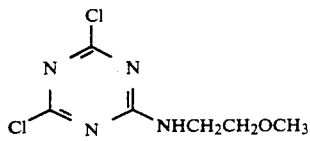

are obtained in form of white crystalline powder; m.p.=73°-75° C. and chlorine content equal to 31.68% (theor. 31.84%).

85 g of a 30% by weight ammonia solution, 250 cc of water and 111.5 g of the intermediate (XVI) are introduced in a 1 liter reactor equipped as in example 1.

The mixture is first heated at 40° C. keeping this temperature for 4 hours, then at 55° C. for 2 hours.

The mass is cooled to 10° C. and the product formed is filtered and washed on the filter with cold water.

By drying the cake in oven at 100° C., 98 g of the intermediate (XVII):

are obtained in form of white crystalline powder; m.p. 195°-197° C. and chlorine content equal to 17.21% (theor.: 17.44%).

The structure of intermediates (XVI) and (XVII) has been further confirmed by IR spectroscopic analysis.

400 cc of water, 81.4 g of the intermediate (XVII) and 42.3 g of 37% by weight hydrochloric acid are introduced in the same 1 liter reactor.

The mixture is heated at 80° C. and is kept at this temperature for 2 hours.

Thereafter, 44.2 g of sodium carbonate dissolved in 200 cc of water are added always at 80° C.

After cooling to room temperature, the product formed is filtered and washed on the filter with water.

By drying the cake in oven at 100° C., 68.1 g of the product:

are obtained in form of white crystalline powder having a m.p. higher than 300° C.

EXAMPLES 6-20

By working under conditions analogous to those described in examples from 1 to 5 products of general formula (I) reported in Table 1 are prepared.

TABLE 1

| Ex. No. | R—N—R$_1$ | | R$_2$—N—R$_3$ | | m.p. (°C.) |
|---|---|---|---|---|---|
| 6 | —N O (morpholino) | | —N O (morpholino) | | >300 |
| 7 | H | CH$_2$CH$_2$CH$_2$OH | CH$_2$CH$_2$CH$_2$OH | H | >300 |
| 8 | H | CH$_2$CH$_2$OCH$_3$ | CH$_2$CH$_2$OCH$_3$ | H | >300 |
| 9 | H | H | —N S (thiomorpholino) | | >300 |
| 10 | H | CH$_2$—CH=CH$_2$ | CH$_2$CH$_2$OH | H | >300 |
| 11 | H | (CH$_2$)$_5$OH | H | | >300 |

TABLE 1-continued

| Ex. No. | R | —N— | R$_1$ | R$_2$ | —N— | R$_3$ | m.p. (°C.) |
|---|---|---|---|---|---|---|---|
| 12 | H | | CH$_2$CHOH—CH$_3$ | CH$_2$CHOH—CH$_3$ | | H | >300 |
| 13 | H | | CH$_2$CH$_2$OCH=CH$_2$ | H | | H | >300 |
| 14 | H | | (CH$_2$)$_2$O(CH$_2$)$_2$OH | (CH$_2$)$_2$O(CH$_2$)$_2$OH | | H | >300 |
| 15 | H | | CH$_2$CH$_2$CH$_2$N(morpholino) | H | | H | >300 |
| 16 | H | | H | piperazinyl (N—NH) | | | >300 |
| 17 | H | | CH$_2$CH$_2$OH | CH$_2$CH$_2$OCH$_3$ | | H | 250–254 |
| 18 | H | | CH$_2$CH$_2$CH$_2$OH | piperidino | | | >300 |
| 19 | H | | cyclohexyl | CH$_2$CH$_2$OH | | H | >300 |
| 20 | H | | (CH$_2$)$_3$OCH$_3$ | (CH$_2$)$_3$OCH$_3$ | | H | >300 |

EXAMPLE 21

75 g of isotactic polypropylene in flakes having a Melt Flow Index equal to 12 and a fraction insoluble in boiling n-heptane equal to 96%, 12 g of the product of example 3, 12 g of ammonium polyphosphate (Exolit 422$^R$ by Hoechst), 0.67 g of dilaurylthiopropionate and 0.33 g of tetra [3-(3,5-diterbutyl-4-hydroxyphenyl)propionate] of pentaerythritol are mixed and molded in a MOORE plate press, working for 7 minutes at a pressure of 40 kg/cm$^2$.

Specimens are obtained in form of little plates having about 3 mm thickness on which the self-estinguishing level is determined by measuring the oxygen index (L.O.I. according to ASTM D-2863/77) in a STANTON REDCROFT apparatus and applying the "Vertical Burning Test" which allows to classify the material at three levels 94 V-0, 94 V-1 and 94 V-2, according to rules UL 94 (edited by "Underwriters Laboratories" USA).

The following results are obtained:

| L.O.I. | = | 32.9 |
|---|---|---|
| UL 94 | : | class V-0 |

We claim:

1. Amelinic compounds of general formula (I):

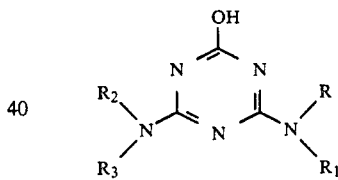

wherein R is hydrogen;
and at least one of radicals from R$_1$ to R$_3$ is:

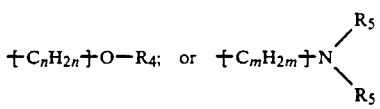

with:
n=integer comprised between 2 and 8;
m=integer comprised between 2 and 6;
the other radicals from R$_1$ to R$_3$, equal or different among them are: H; (C$_1$–C$_{18}$)-alkyl; (C$_2$–C$_8$)-alkenyl; (C$_6$–C$_{16}$)-cycloalkyl or (C$_6$–C$_{16}$)-alkylcycloalkyl, optionally substituted by a hydroxyl or (C$_1$–C$_4$)-hydroxyalkyl function;
R$_4$=H; (C$_1$–C$_8$)-alkyl; (C$_2$–C$_6$)-alkenyl; [C$_p$H$_{2p}$]O—R$_6$, wherein p is an integer comprised between 1 and 4 and R$_6$ is H or (C$_1$–C$_4$)-alkyl; (C$_6$–C$_{12}$)-cycloalkyl or (C$_6$–C$_{12}$)-alkylcycloalkyl;
radicals R$_5$, equal or different between them, are H; (C$_1$–C$_8$)-alkyl; (C$_2$–C$_6$)-alkenyl; (C$_6$–C$_{12}$)-cycloalkyl or (C$_6$–C$_{12}$)-alkylcycloalkyl; (C$_1$–C$_4$)-hydroxyalkyl; or the group:

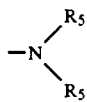

is replaced by aziridino, pyrrolidino, piperidino, morpholino, thiomorpholino, piperazino, 4-methylpiperazino or 4-ethylpiperazino;
or in the general formula (I) at least one of groups:

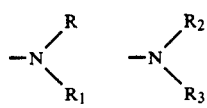

is replaced by aziridino, pyrrolidino, piperidino, morpholino, thiomorpholino, piperazino, 4-methylpiperazino, 4-ethylpiperazino, 2-methylpiperazino, 2,5-dimethylpiperazino, 2,3,5,6-tetramethylpiperazino, 2,2,5,5-tetramethylpiperazino, 2-ethylpiperazino or 2,5-diethylpiperazino
provided that when $R_2$ and $R_3$ are equal to H, $R_1$ is different from 2-hydroxyethyl.

2. Amelinic compounds according to claim 1, wherein one or both of the groups:

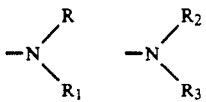

in Formula (I) is (are) replaced by morpholino.

3. Amelinic compounds according to claim 1 or 2, wherein the group:

is replaced by morpholino.

* * * * *